(12) United States Patent
Tornqvist

(10) Patent No.: US 10,398,834 B2
(45) Date of Patent: Sep. 3, 2019

(54) DEVICE, SEALING MEMBER AND FLUID CONTAINER

(75) Inventor: Hakan Tornqvist, Särö (SE)

(73) Assignee: Carmel Pharma AB, Göteborg (SE)

( * ) Notice: Subject to any disclaimer, the term of this patent is extended or adjusted under 35 U.S.C. 154(b) by 621 days.

(21) Appl. No.: 11/847,518

(22) Filed: Aug. 30, 2007

(65) Prior Publication Data

US 2009/0057258 A1 Mar. 5, 2009

(51) Int. Cl.
| | | |
|---|---|---|
| *A61M 5/162* | (2006.01) | |
| *A61J 1/20* | (2006.01) | |
| *A61M 39/10* | (2006.01) | |

(52) U.S. Cl.
CPC ............... *A61M 5/162* (2013.01); *A61J 1/20* (2013.01); *A61M 39/1011* (2013.01); *A61J 1/201* (2015.05); *A61J 1/2055* (2015.05)

(58) Field of Classification Search
CPC .... A61J 1/20; A61J 1/22; A61J 1/2096; A61J 2001/201; A61M 5/162; A61M 39/045; A61M 2205/195; Y10S 215/03; Y10S 604/905
USPC ..... 215/247, 249, 297, 391; 604/403; 5/247, 5/249, 297, 391
See application file for complete search history.

(56) References Cited

U.S. PATENT DOCUMENTS

| | | |
|---|---|---|
| 1,844,342 A | 2/1932 | Berman |
| 2,010,417 A | 8/1935 | Schwab |
| 2,697,438 A | 12/1954 | Hickey |
| 2,717,599 A | 9/1955 | Huber |
| 2,954,768 A * | 10/1960 | Hamilton ............... A61M 5/162 604/274 |
| 3,064,651 A | 11/1962 | Henderson |
| 3,071,135 A | 1/1963 | Baldwin et al. |
| 3,308,822 A | 3/1967 | DeLuca |
| 3,316,908 A | 5/1967 | Burke |
| 3,340,671 A | 9/1967 | Loo |
| 3,390,677 A | 7/1968 | Razimbaud |
| 3,448,740 A | 6/1969 | Figge |
| 3,542,240 A | 11/1970 | Solowey |

(Continued)

FOREIGN PATENT DOCUMENTS

| | | |
|---|---|---|
| AU | 200112863 | 5/2003 |
| DE | 2005519 | 10/1979 |

(Continued)

OTHER PUBLICATIONS

Taiwan Search Report for Taiwan Patent Application 092106323 dated Mar. 21, 2003 (4 pages).

(Continued)

*Primary Examiner* — Andrew T Kirsch
(74) *Attorney, Agent, or Firm* — Servilla Whitney LLC

(57) ABSTRACT

A device for transferring a fluid to and/or from a fluid container having a sealing member. The device includes a piercing member for penetrating the sealing member and an elongated body defining a longitudinal flow channel through which a fluid may flow into and/or out of the fluid container and at least one opening that communicates with the flow channel. The at least one opening is arranged to extend along at least 1% of the length (l) of the piercing member to ensure that at least part of the at least one opening (20) is located substantially adjacent to the innermost side of a sealing member when the device is in use.

19 Claims, 3 Drawing Sheets

(56) References Cited

U.S. PATENT DOCUMENTS

| | | | |
|---|---|---|---|
| 3,783,895 A | 1/1974 | Weichselbaum | |
| 3,788,320 A | 1/1974 | Dye | |
| 3,822,700 A | 7/1974 | Pennington | |
| 3,938,520 A | 2/1976 | Scislowicz et al. | |
| 3,976,073 A | 8/1976 | Quick et al. | |
| 4,056,116 A * | 11/1977 | Carter et al. | 137/68.3 |
| 4,058,121 A * | 11/1977 | Choksi | A61J 1/2096 604/274 |
| 4,096,860 A | 6/1978 | McLaughlin | |
| 4,296,786 A | 10/1981 | Brignola | |
| D270,568 S | 9/1983 | Armstrong | |
| 4,457,749 A * | 7/1984 | Bellotti | A61M 39/221 604/244 |
| 4,490,139 A | 12/1984 | Huizenga et al. | |
| 4,516,967 A * | 5/1985 | Kopfer | 604/87 |
| 4,564,054 A | 1/1986 | Gustavsson | |
| 4,573,967 A | 3/1986 | Hargrove et al. | |
| 4,576,211 A | 3/1986 | Valentini et al. | |
| 4,581,016 A | 4/1986 | Gettig | |
| 4,582,223 A | 4/1986 | Kobe | |
| 4,588,403 A | 5/1986 | Weiss et al. | |
| 4,600,040 A | 7/1986 | Naslund | |
| 4,623,343 A | 11/1986 | Thompson | |
| 4,629,455 A | 12/1986 | Kanno | |
| 4,632,673 A | 12/1986 | Tiitola et al. | |
| 4,636,204 A | 1/1987 | Christopherson et al. | |
| 4,673,400 A | 6/1987 | Martin | |
| 4,673,404 A | 6/1987 | Gustavsson | |
| 4,737,150 A | 4/1988 | Baeumle et al. | |
| 4,752,287 A | 6/1988 | Kurtz et al. | |
| 4,759,756 A | 7/1988 | Forman et al. | |
| 4,768,568 A | 9/1988 | Fournier et al. | |
| 4,792,329 A | 12/1988 | Schreuder | |
| 4,804,015 A | 2/1989 | Albinsson | |
| 4,822,340 A | 4/1989 | Kamstra | |
| 4,826,492 A | 5/1989 | Magasi | |
| 4,834,717 A | 5/1989 | Haber et al. | |
| 4,842,585 A | 6/1989 | Witt | |
| 4,850,978 A | 7/1989 | Dudar et al. | |
| 4,864,717 A | 9/1989 | Baus, Jr. | |
| 4,872,494 A | 10/1989 | Coccia | |
| 4,878,897 A | 11/1989 | Katzin | |
| 4,889,529 A | 12/1989 | Haindl | |
| 4,898,209 A | 2/1990 | Zbed | |
| 4,909,290 A | 3/1990 | Coccia | |
| 4,932,937 A | 6/1990 | Gustavsson et al. | |
| 4,944,736 A * | 7/1990 | Holtz | 604/403 |
| 4,964,855 A | 10/1990 | Todd et al. | |
| 4,982,769 A | 1/1991 | Fournier et al. | |
| 4,994,048 A | 2/1991 | Metzger | |
| 4,997,083 A | 3/1991 | Loretti et al. | |
| 5,017,186 A | 5/1991 | Arnold | |
| 5,041,105 A | 8/1991 | D'Alo et al. | |
| 5,061,264 A | 10/1991 | Scarrow | |
| 5,071,413 A | 12/1991 | Utterberg | |
| 5,122,116 A | 6/1992 | Kriesel et al. | |
| 5,122,123 A | 6/1992 | Vaillancourt | |
| 5,137,524 A | 8/1992 | Lynn et al. | |
| 5,158,554 A | 10/1992 | Jepson et al. | |
| 5,176,673 A | 1/1993 | Marrucchi | |
| 5,199,947 A | 4/1993 | Lopez et al. | |
| 5,201,725 A | 4/1993 | Kling | |
| 5,207,658 A | 5/1993 | Rosen et al. | |
| 5,232,109 A | 8/1993 | Tirrell et al. | |
| 5,254,097 A | 10/1993 | Schock et al. | |
| 5,279,576 A | 1/1994 | Loo et al. | |
| 5,279,583 A | 1/1994 | Shober, Jr. et al. | |
| 5,279,605 A | 1/1994 | Karrasch et al. | |
| 5,308,347 A | 5/1994 | Sunago et al. | |
| 5,312,366 A | 5/1994 | Vailancourt | |
| 5,328,480 A | 7/1994 | Melker et al. | |
| 5,334,163 A | 8/1994 | Sinnett | |
| 5,356,406 A * | 10/1994 | Schraga | 604/415 |
| 5,385,545 A | 1/1995 | Kriesel et al. | |
| 5,385,547 A | 1/1995 | Wong et al. | |
| 5,389,085 A | 2/1995 | D'Alessio et al. | |
| 5,405,326 A | 4/1995 | Haber et al. | |
| 5,445,630 A | 8/1995 | Richmond | |
| 5,447,501 A | 9/1995 | Karlsson et al. | |
| 5,456,675 A | 10/1995 | Wolbring et al. | |
| 5,470,522 A | 11/1995 | Thome et al. | |
| 5,478,328 A * | 12/1995 | Silverman et al. | 604/272 |
| 5,478,337 A | 12/1995 | Okamoto et al. | |
| 5,492,531 A | 2/1996 | Post et al. | |
| 5,514,117 A | 5/1996 | Lynn | |
| 5,515,871 A | 5/1996 | Bittner et al. | |
| 5,536,259 A | 7/1996 | Utterberg | |
| 5,575,780 A | 11/1996 | Saito | |
| 5,593,028 A | 1/1997 | Haber et al. | |
| 5,613,954 A | 3/1997 | Nelson et al. | |
| 5,632,735 A | 5/1997 | Wyatt et al. | |
| 5,647,845 A | 7/1997 | Haber et al. | |
| 5,685,866 A | 11/1997 | Lopez | |
| 5,752,942 A | 5/1998 | Doyle et al. | |
| 5,766,147 A | 6/1998 | Sancoff et al. | |
| 5,766,211 A | 6/1998 | Wood et al. | |
| 5,782,872 A | 7/1998 | Muller | |
| 5,795,336 A | 8/1998 | Romano et al. | |
| 5,817,083 A | 10/1998 | Shemesh et al. | |
| 5,820,609 A | 10/1998 | Saito | |
| 5,827,262 A | 10/1998 | Neftel et al. | |
| 5,837,262 A | 11/1998 | Golubev et al. | |
| 5,875,931 A | 3/1999 | Py | |
| 5,879,345 A | 3/1999 | Aneas | |
| 5,897,526 A | 4/1999 | Vaillancourt | |
| 5,934,510 A | 8/1999 | Anderson | |
| 5,984,899 A | 11/1999 | D'Alessio et al. | |
| 6,063,068 A | 5/2000 | Fowles et al. | |
| D427,308 S | 6/2000 | Zinger | |
| 6,070,623 A | 6/2000 | Aneas | |
| 6,071,270 A | 6/2000 | Fowles et al. | |
| 6,090,091 A | 7/2000 | Fowles et al. | |
| 6,113,068 A | 9/2000 | Ryan | |
| 6,113,583 A * | 9/2000 | Fowles et al. | 604/403 |
| 6,142,446 A | 11/2000 | Leinsing | |
| 6,146,362 A | 11/2000 | Turnbull et al. | |
| 6,209,738 B1 | 4/2001 | Jansen et al. | |
| 6,221,065 B1 | 4/2001 | Davis | |
| D445,501 S | 6/2001 | Niedospial, Jr. | |
| 6,245,056 B1 | 6/2001 | Walker et al. | |
| 6,253,804 B1 | 7/2001 | Safabash | |
| 6,258,078 B1 | 7/2001 | Thilly | |
| 6,387,074 B1 | 5/2002 | Horppu et al. | |
| 6,453,956 B2 | 9/2002 | Safabash | |
| 6,471,674 B1 | 10/2002 | Emig et al. | |
| 6,517,523 B1 | 2/2003 | Kaneko et al. | |
| 6,537,263 B1 | 3/2003 | Aneas | |
| 6,571,837 B2 | 6/2003 | Jansen et al. | |
| 6,591,876 B2 | 7/2003 | Safabash | |
| 6,644,367 B1 | 11/2003 | Savage et al. | |
| 6,685,692 B2 | 2/2004 | Fathallah | |
| 6,715,520 B2 | 4/2004 | Andreasson et al. | |
| 6,761,286 B2 | 7/2004 | Py et al. | |
| D495,416 S | 8/2004 | Dimeo et al. | |
| 6,786,244 B1 | 9/2004 | Jones | |
| D506,256 S | 6/2005 | Miyoshi et al. | |
| 6,960,194 B2 | 11/2005 | Hommann et al. | |
| 7,000,806 B2 | 2/2006 | Py et al. | |
| 7,080,672 B2 | 7/2006 | Fournier et al. | |
| 7,297,140 B2 | 11/2007 | Orlu et al. | |
| D570,477 S | 6/2008 | Gallogly et al. | |
| D572,820 S | 7/2008 | Gallogly et al. | |
| D577,438 S | 9/2008 | Gallogly et al. | |
| D577,822 S | 9/2008 | Gallogly et al. | |
| D582,033 S | 12/2008 | Baxter et al. | |
| D605,755 S | 12/2009 | Baxter et al. | |
| 7,703,486 B2 | 4/2010 | Costanzo | |
| D616,984 S | 6/2010 | Gilboa | |
| 7,744,581 B2 | 6/2010 | Wallen et al. | |
| 2001/0021825 A1 | 9/2001 | Becker et al. | |
| 2001/0025671 A1 | 10/2001 | Safabash | |
| 2002/0002352 A1 | 1/2002 | Becker et al. | |
| 2002/0022804 A1 | 2/2002 | Connolly et al. | |
| 2002/0082586 A1 | 6/2002 | Finley et al. | |

(56) References Cited

U.S. PATENT DOCUMENTS

| | | |
|---|---|---|
| 2002/0127150 A1 | 9/2002 | Sasso |
| 2002/0177819 A1 | 11/2002 | Barker et al. |
| 2003/0010717 A1 | 1/2003 | Brugger et al. |
| 2003/0070726 A1 | 4/2003 | Andreasson et al. |
| 2003/0106610 A1 | 6/2003 | Roos et al. |
| 2003/0107628 A1 | 6/2003 | Fowles et al. |
| 2003/0199846 A1 | 10/2003 | Fowles et al. |
| 2003/0233083 A1 | 12/2003 | Houwaert et al. |
| 2004/0116858 A1 | 6/2004 | Heinz et al. |
| 2004/0199139 A1 | 10/2004 | Fowles et al. |
| 2004/0215147 A1 | 10/2004 | Wessman et al. |
| 2005/0215977 A1 | 9/2005 | Uschold |
| 2005/0228309 A1* | 10/2005 | Fisher .............. A61B 17/00491 600/562 |
| 2006/0025747 A1 | 2/2006 | Sullivan et al. |
| 2006/0106360 A1 | 5/2006 | Wong |
| 2006/0111667 A1 | 5/2006 | Matsurra et al. |
| 2006/0157984 A1 | 7/2006 | Rome et al. |
| 2006/0186045 A1 | 8/2006 | Jensen et al. |
| 2006/0200095 A1* | 9/2006 | Steube ................. A61J 1/2096 604/272 |
| 2007/0021725 A1 | 1/2007 | Villette |
| 2007/0060841 A1 | 3/2007 | Henshaw |
| 2007/0088313 A1 | 4/2007 | Zinger et al. |
| 2007/0106244 A1 | 5/2007 | Mosler et al. |
| 2007/0156112 A1 | 7/2007 | Walsh et al. |
| 2007/0179441 A1 | 8/2007 | Chevallier |
| 2007/0270759 A1 | 11/2007 | Pessin |
| 2007/0270778 A9 | 11/2007 | Zinger et al. |
| 2008/0045919 A1 | 2/2008 | Jakob et al. |
| 2008/0103453 A1 | 5/2008 | Liversidge |
| 2008/0103485 A1 | 5/2008 | Kruger |
| 2008/0172039 A1 | 7/2008 | Raines |
| 2008/0223484 A1 | 9/2008 | Horppu |
| 2008/0287920 A1 | 11/2008 | Fangrow et al. |
| 2008/0312634 A1 | 12/2008 | Helmerson et al. |
| 2009/0254042 A1 | 10/2009 | Gratwohl et al. |
| 2010/0137827 A1 | 6/2010 | Warren et al. |
| 2010/0204671 A1 | 8/2010 | Kraushaar et al. |
| 2010/0243099 A1 | 9/2010 | Yodfat |

FOREIGN PATENT DOCUMENTS

| | | |
|---|---|---|
| EP | 0255025 | 2/1988 |
| EP | 0259582 | 3/1988 |
| EP | 0285424 | 10/1988 |
| EP | 0311787 | 4/1989 |
| EP | 0376629 | 7/1990 |
| EP | 0803267 | 10/1997 |
| EP | 0819442 | 1/1998 |
| EP | 0995453 | 4/2000 |
| EP | 1060730 | 12/2000 |
| EP | 1484073 | 12/2004 |
| EP | 1731128 | 12/2006 |
| FR | 2757405 | 6/1998 |
| FR | 2780878 | 1/2000 |
| GB | 1579065 | 11/1980 |
| JP | 53-122369 | 3/1952 |
| JP | 49-12690 | 5/1972 |
| JP | 55-81659 | 6/1980 |
| JP | 59-30243 | 2/1984 |
| JP | 288664 | 7/1990 |
| JP | 04-156849 | 5/1992 |
| JP | 06-099997 | 4/1994 |
| JP | 3030963 | 8/1996 |
| JP | 2000167022 | 6/2000 |
| JP | 2001505092 | 4/2001 |
| JP | 2001293085 | 10/2001 |
| JP | 2003-0033423 | 2/2003 |
| JP | 2003-062068 | 3/2003 |
| JP | 2004-313808 | 11/2004 |
| JP | 2006-314570 | 11/2006 |
| TW | 482670 | 4/2002 |
| WO | WO 1984/04672 | 12/1984 |
| WO | WO 1984/04673 | 12/1984 |
| WO | WO 1990/03536 | 4/1990 |
| WO | WO 1998/19724 | 5/1998 |
| WO | WO 1999/27886 | 6/1999 |
| WO | WO 1999/62578 | 12/1999 |
| WO | WO 2000/05292 | 2/2000 |
| WO | WO 2000/35517 | 6/2000 |
| WO | WO 2001/80928 | 11/2001 |
| WO | WO 2002/02048 | 1/2002 |
| WO | WO 2002/11794 | 2/2002 |
| WO | WO 2002/064077 | 8/2002 |
| WO | WO 2002/076540 | 10/2002 |
| WO | WO2005074860 | 8/2005 |
| WO | WO 2006/082350 | 8/2006 |
| WO | WO 2006/083333 | 8/2006 |
| WO | WO2006138184 | 12/2006 |
| WO | WO 2008/115102 | 9/2008 |

OTHER PUBLICATIONS

Japan Application No. 2003-583539, Official Action dated May 1, 2009 (3 pages).

Japan Application No. 2003-577789, Official Action dated Feb. 24, 2009 (4 pages).

International Search Report, PCT/EP2008/067535 dated Oct. 13, 2009 (3 pages).

International Search Report, PCT/EP2008/067522 dated Aug. 12, 2009 (2 pages).

* cited by examiner

DEVICE, SEALING MEMBER AND FLUID CONTAINER

TECHNICAL FIELD

The present invention concerns a device for transferring a fluid to and/or from a fluid container having a sealing member. The present invention also concerns a sealing member and a fluid container. The device, sealing member and fluid container of the present invention are particularly, but not exclusively intended for transferring medical substances to and/or from a fluid container, however they may be used for transferring any kind of fluid, i.e. any continuous, amorphous substance whose molecules move freely past one another and that has the tendency to assume the shape of its container, to and/or from a fluid container.

BACKGROUND

Medical drugs and solvents are often supplied in glass or plastic containers, such as vials, bottles or bags, which are sealed by a rubber, plastic or elastomeric bung, stopper, membrane or puncturable cap. Such sealing members prevent deterioration or contamination of the drug, allow the contents of a container to be mixed by shaking, and prevent the contents of the container from leaking out and contaminating the surroundings. A cannula or a hollow spike comprising a flow channel and an opening that communicates with the flow channel, is usually inserted through such a sealing member to supply fluids to the container and to withdraw fluid therefrom.

If an infusion fluid container is made of a rigid or semi-rigid material, i.e. if its walls are non-collapsible, an air inlet is required to withdraw medical fluid from the infusion fluid container and prevent the formation of a vacuum therein. When withdrawing fluid from a rigid or semi-rigid infusion fluid container, a spike having a medical fluid flow channel and an air inlet passage, usually comprising an air filter, is therefore used.

When a container comprising medical fluid is nearly empty a cannula or spike is often used to withdraw the last few drops of the medical fluid (which may be very expensive and/or toxic) from the container to minimize waste and to facilitate cleaning/disposal of the container. The cannula or spike is slowly and carefully retracted through the sealing member while withdrawing the medical fluid remaining in the container. However, a toxic drug may leak out and contaminate the surroundings during such a procedure and non-filtered air containing undesirable particles such as dust, pollen or bacteria may be drawn into the cannula and thus contaminate the medical fluid therein.

In some cases containers are in fact provided with an extra amount of the drug that is to be withdrawn to allow for the fact that not all of the drug will be withdrawn from the container. A user is then able to withdraw the recommended number of doses from the container but doing so will increase the cost of each container of medical fluid, increase waste and make cleaning or disposal of the container more complex.

Since sealing members are available in a wide variety of configurations, sizes and thicknesses, it is difficult to design a spike that is suitable for use with a plurality of different sealing members and which makes it possible to withdraw the last few drops of a medical fluid out of the containers in a safe and convenient way.

SUMMARY OF THE INVENTION

One aspect of the invention features a device that enables an efficient transfer of fluid into and/or out of a fluid container having a sealing member.

According to one embodiment, a device comprises a piercing member for penetrating the sealing member and an elongated body defining a longitudinal flow channel through which a fluid may flow into or out of the fluid container. The device comprises at least one opening that communicates with the flow channel whereby the at least one opening is arranged to extend along at least 1% preferably at least 2%, or at least 3%, or at least 4%, or at least 5%, or at least 10%, or at least 20%, or at least 30%, or at least 50% or most preferably at least 70% or 100% of the length of the piercing member to ensure that at least part of the at least one opening is located substantially adjacent to the innermost side of a sealing member when the device is in use.

The length of the piercing member is defined as the distance from the tip of the piercing member to the point at which the width of the device increases by an amount that would require a substantially increased force to push that part of the device more deeply into an infinitely wide sealing member of a bottomless fluid container. In cases where the device has a substantially uniform cross section along its entire length, the length of the piercing member is defined as the distance from the tip of the piercing member to opposite end of the device.

Such a device allows the entire contents, or essentially the entire contents of the fluid container to be drained from an inverted fluid container.

The inventive device also improves the mixing of fluids inside the container when the fluid container is inverted or in an upright position. If a liquid drug is to be mixed with a liquid solvent in an inverted or upright fluid container, for example, the mixing of the two liquids is facilitated since a plurality of openings or an elongated opening allows a liquid drug/solvent to flow into the fluid container more quickly than if using a conventional device and mixing is improved due to the increased and more distributed inlet area and the increased turbulence caused thereby.

Furthermore, if the fluid container and its contents have been refrigerated, if a fluid having a higher temperature than the contents of the fluid container is supplied through the sealing member of an inverted fluid container, convection currents may speed up the mixing of the two fluids. Convection currents may also aid mixing if a refrigerated fluid enters the top of an upright fluid container containing a fluid having a higher temperature than the refrigerated fluid.

The inventive device is suitable for use with a plurality of fluid containers comprising sealing members of different thicknesses (which can range from a few millimeters to a few centimeters) and different configurations (such as concave, biconcave or M-shaped) if the at least one opening extends over a length that is greater than the thickness of the thickest sealing member that the device is designed to penetrate.

According to an embodiment of the invention the device comprises one opening that extends substantially along the entire length of the piercing member.

According to another embodiment of the invention the device comprises a plurality of openings that are uniformly or non-uniformly spaced along the length of the piercing member.

According to a further embodiment of the invention the device comprises a retractable sleeve, such as a rubber, plastic or elastomeric sheath, that is arranged to at least partially cover and seal the at least one opening before the device is inserted into the sealing member of a fluid container. The retractable sleeve is arranged to abut against the outermost side of the sealing member when the device has been inserted into a sealing member of a fluid container and retract as the piercing member penetrates more deeply into the sealing member so that it will cover and seal only the part of the opening, or the openings that are located outwards of the outermost side of the sealing member when the device is in use and thus prevent any medical fluid from leaking out of that opening or those openings.

According to an embodiment of the invention the device comprises connecting means to connect it to a fluid container so that the device will not accidentally become detached from the fluid container when the device is in use, or prior to or after use.

According to an embodiment of the invention, the device comprises a ruled scale, which for example extends from the outermost edge of an opening in the direction from the interior of the fluid container outwards towards the sealing member. If the thickness of a sealing member at the point of insertion of the device is known, the ruled scale may be used to indicate to a user how far the device has to be inserted into the sealing member to ensure that the outermost edge of the opening becomes located substantially adjacent to the innermost side of a sealing member when the device is in use. The ruled scale may also be used to measure the thickness of the sealing member before the device is inserted into it.

The present invention also concerns a sealing member, such as a rubber, plastic or elastomeric bung, stopper, membrane or puncturable cap, for sealing an outlet of a fluid container, which sealing member comprises a device according to any of the embodiments of the invention whereby the device is integrally formed with the sealing member or releasably/non-releasably connected thereto.

According to an embodiment of the invention the device is slidably mounted on the sealing member so that the at least one opening of the device may be opened and closed by sliding the device back and forth with respect to the sealing member.

The present invention further concerns a fluid container that comprises a sealing member according to any of the embodiments of the invention.

BRIEF DESCRIPTION OF THE DRAWINGS

The present invention will hereinafter be further explained by means of non-limiting examples with reference to the appended figures where.

It should be noted that the drawings have not been drawn to scale and that the dimensions of certain features have been exaggerated for the sake of clarity.

Furthermore, it should be noted that irrespective of whether a rigid, semi-rigid or flexible fluid container is exemplified in the appended figures, the present invention is suitable for use with any type of fluid container having a sealing member.

DETAILED DESCRIPTION OF EMBODIMENTS

Figure 1:
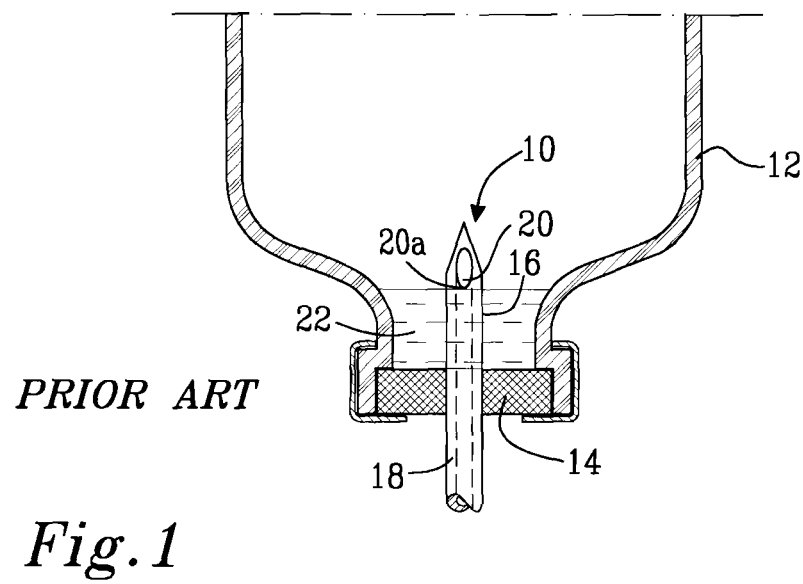
FIG. 1 shows a conventional device for transferring fluid to and/or from a fluid container.

FIG. 1 shows a conventional device 10 for transferring fluid to and/or from an inverted fluid container 12 having a sealing member 14 that hermetically seals the contents 22 of the fluid container 12. The device 10 comprises a piercing member 16 for penetrating the sealing member 14 and an elongated body defining a longitudinal flow channel 18 through which the contents of the fluid container may flow into and/or out of the fluid container 12 and one lateral opening that communicates with the flow channel 18. Since sealing members 14 vary in thickness and toughness, the opening 20 of the device can become located at any of an infinite number of positions in the fluid container 12 depending on how much force the user applies when inserting the device 10 through the sealing member 14 and depending on whether the device is inserted substantially vertically or at an angle to the longitudinal axis of the fluid container 12. Once the contents 22 of the fluid container 12 have drained to a level just under the outermost edge 20*a* of the opening, no more fluid will be able to drain from the fluid container unless the device is withdrawn slightly.

Figure 2:
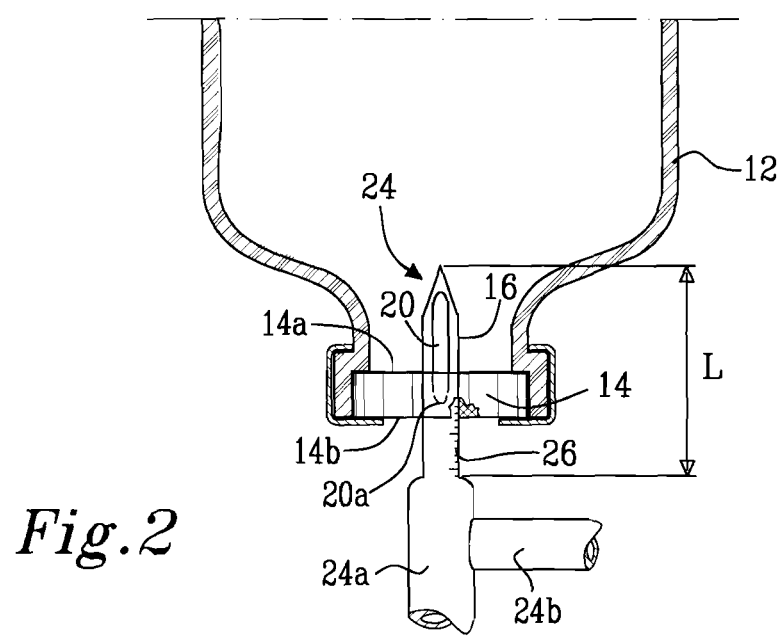
FIGS. 2-5 show devices for transferring fluid to and/or from a fluid container according to embodiments of the invention.

FIG. 2 shows a device 24 in accordance with the present invention for transferring a fluid to and/or from an inverted fluid container 12 having a sealing member 14. The device 24 comprises a piercing member 16 having a bevelled tip for penetrating the sealing member 14 and may also optionally comprise an elongated tubular body portion 24*a* of any symmetrical or non-symmetrical cross-sectional form, such as circular, square, hexagonal or octagonal. The elongated body portion 24*a* has a greater width than the width of the piercing member 16 and is not intended to be inserted through the sealing member 14 of a fluid container 12. The elongated body portion 24*a* may comprise a drop chamber. The device 24 may also optionally comprise an air/liquid inlet 24*b*.

The piercing member 16 defines a substantially longitudinal flow channel (not shown) through which the contents of the fluid container may flow into and/or out of the fluid container 12 and one elongated opening 20, that can be of any shape, such as rectangular, square, circular or oval, which communicates with the flow channel. The opening 20, extends longitudinally along about 50% of the length, L, of the piercing member 16, either from the tip of the piercing member or a few millimeters from the tip of the piercing member, to ensure that at least part of the at least one opening is located substantially adjacent to the innermost side 14*a* of a sealing member 14 when the device 10 is in use. The maximum width of the opening 20 is equal to at least 20% of the maximum width of the piercing member 16, preferably at least 50% of the maximum width of the piercing member 16.

In the example shown, the innermost side 14*a* of the sealing member 14 overlaps the elongated opening 20 when the device is in use. The device 24 also comprises a ruled scale 26 to allow a user to accurately position the outermost edge 20*a* of the opening 20 if he/she knows the thickness of the sealing member 14 at the point of insertion of the device 24.

The device 24 may comprise plastic, such as thermoplastic material; metal, glass or a ceramic material. The length of the piercing member 16 may range from 0.5-5.0 cm or more, whereby the length of the piercing member is preferably 5 to 20 times its maximum width.

It should be noted that although a rigid or semi-rigid fluid container 12, such as a glass bottle, has been illustrated in FIG. 2, the inventive device 24 is equally suitable for use with a non-rigid fluid container, such as an infusion bag. Furthermore, even though an air inlet would be necessary when draining fluid from a rigid or semi-rigid fluid container, air inlets and air channels have not been illustrated in any of the drawings for the sake of clarity. The inventive device could however comprise any number of channels for air or other fluids.

Figure 3:
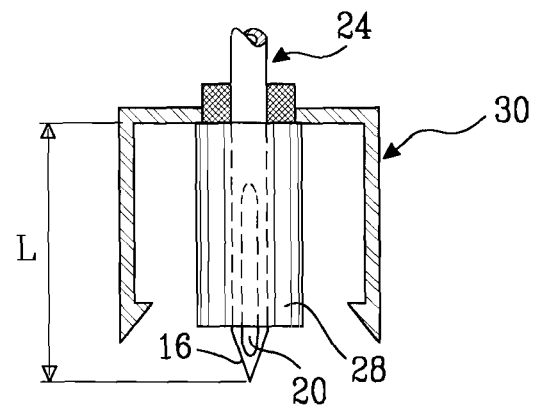

FIG. 3 shows a device 24 according to another embodiment of the invention before the device has been inserted into the sealing member of a fluid container. The device comprises one opening 20 that extends substantially along the entire length, L, of the piercing member 16 from behind its solid beveled tip towards the opposite end of the piercing member 16. The length of the opening 20 will of course depend on the thickness of the thickest sealing member 14 that it is intended to penetrate. The device 24 comprises a tightly fitting elastic retractable sleeve 28, comprising silicone rubber for example, that is arranged to at least partially cover and seal the at least one opening 20 before the device is inserted into a fluid container. The retractable sleeve 28 is arranged to abut against the outermost side 14b of the sealing member 14 when the device has been inserted into a fluid container 12 and to retract as the piercing member 16 penetrates more deeply into sealing member 14.

Figure 4:
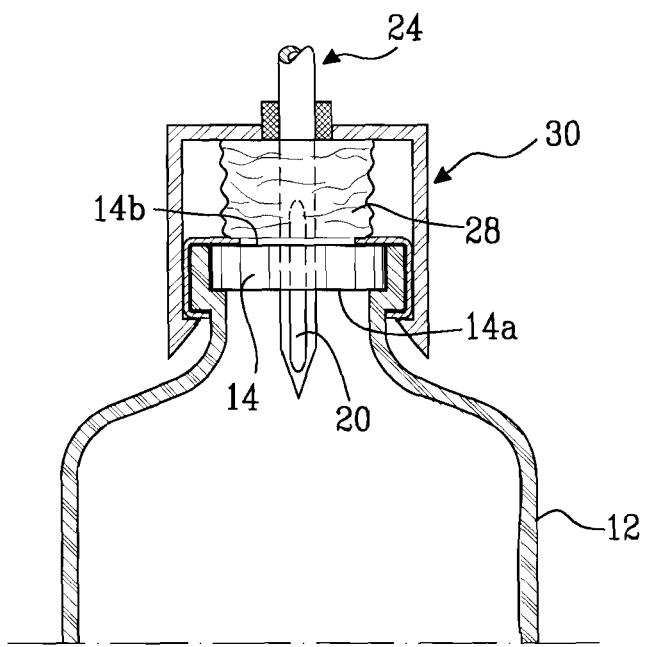

FIG. 4 shows the device 24 of FIG. 3 after it has been inserted into the sealing member 14 of a fluid container 12. It can be seen that the part of the opening 20 inwards of the innermost side 14a of the sealing member 14 is exposed to the interior of the fluid container whereas the part of the opening 20 outwards of the outermost side 14b of the sealing member 14 is sealed, thereby preventing deterioration or contamination of the contents of the fluid container 12, allowing the contents of a fluid container 12 to be mixed by shaking, and preventing the contents of the fluid container 12 from leaking out and contaminating the surroundings.

The device 24 shown in FIGS. 3 and 4 also comprises connecting means 30, to grippingly engage the rim of the fluid container 12 to hold the device 24 firmly in place on the fluid container 12. The connecting means 30 comprises two manually operable resilient arms comprising curved end regions that slidably engage the rim of the fluid container 12 when the device 24 has been pushed through the fluid container's sealing member 14. The connecting means 30, which may be a snap-fit mechanism, a luer lock or any other mechanical or non-mechanical connecting means, may be arranged to cause the piercing member 16 of the device to penetrate the sealing member 14 of a fluid container 12 as the connecting means are engaged, thus providing fluid communication between the interior of the fluid container 12 and the flow channel of the device 24, i.e. fluid communication is provided when a luer lock is twisted into a locked position for example.

According to another embodiment of the invention, the device comprises a piercing member shield/guard to prevent users from being hurt by the piercing member 16 and to prevent contamination of the piercing member 16. In the embodiment shown in FIGS. 3 and 4, the connecting means 30 also act as a piercing member shield/guard.

It should be noted that the at least one opening 20 of the inventive device 24 need not necessarily extend in a direction parallel or collinear to the longitudinal axis of the device 24, it/they may extend in a zig-zag pattern along the length of the piercing member 16 or even be constituted by a plurality of openings that extend transversely to the longitudinal axis of the device 24.

Figure 5:
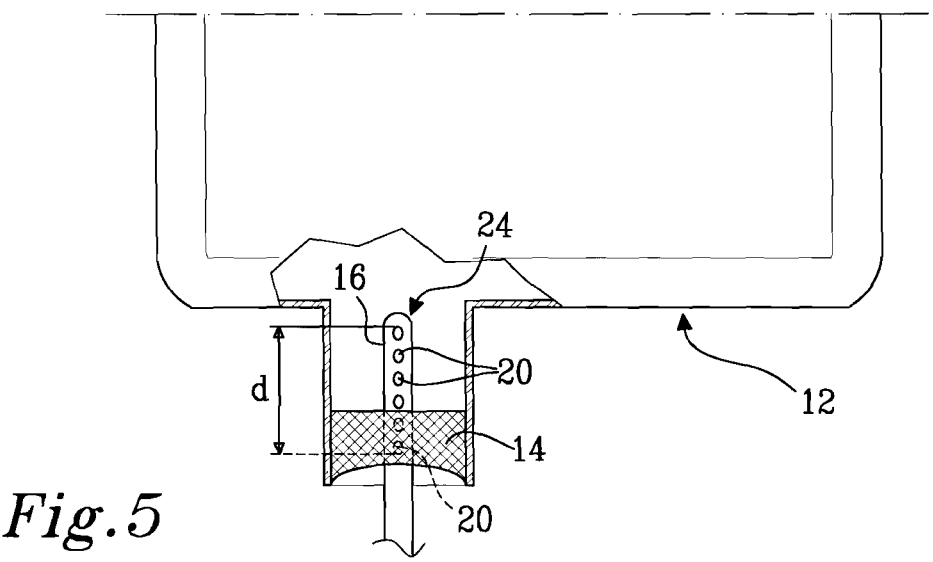

FIG. 5 shows a device 24 according to a further embodiment of the invention. The device 24 comprises a plurality of openings 20 uniformly spaced along a distance d, which extents substantially along the entire length of the piercing member 16. If the length of the piercing member is 3 cm, the device 24 may for example comprise ten uniformly spaced openings 20 that extend 2 mm along the longitudinal direction of the piercing member 16, each thereby spaced 1 mm apart. In the illustrated embodiment the piercing member 16 comprises a blunt end, which may be used to pierce a sealing member 14 having a thin central portion, or to pierce a pre-slit sealing member 14. It is to be understood, of course, that a pointed piercing member may also be used in relation to this embodiment.

Figure 6:
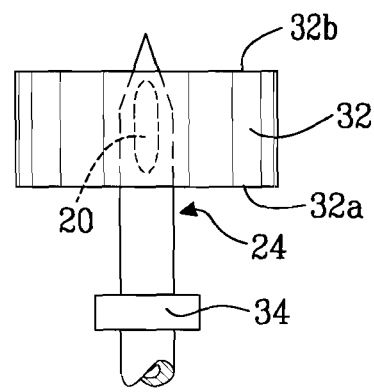
FIGS. 6-7 show sealing a sealing member according to an embodiment of the invention.
Figure 7:
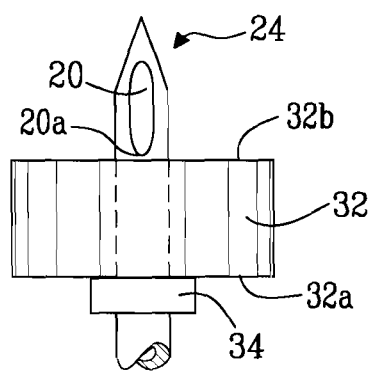

FIGS. 6 and 7 show a sealing member 32 according to an embodiment of the invention. The sealing member 32 comprises natural or synthetic rubber or any other elastomer, plastic or glass for example. The sealing member 32 comprises a device 24 according to any of the embodiments of the invention whereby the device 24 is integrally formed with the sealing member 32 or releasably/non-releasably connected thereto. The device 24 is slidably mounted on the sealing member 32 so that the at least one opening 20 of the device may be opened and closed by sliding the device back and forth with respect to the sealing member from a closed position as shown in FIG. 6 to an open position as shown in FIG. 7. The device 24 may of course be arranged to stop at any number of further positions in addition to the fully open and fully closed positions that have been illustrated.

In FIG. 7, the entire piercing member 16 of the device 24 has been pushed through the sealing member 32 until a shoulder 34 on the device abuts against the outermost edge 32a of the sealing member 32. In this position the lower edge 20a of the opening is aligned with the innermost edge 32b of the sealing member 32 so that the whole opening 20 will be exposed to the interior of the fluid container in which the sealing member 32 is inserted.

The inventive sealing member 32 may be inserted into the inlet/outlet of a fluid container 12 or may comprise means, such as a thread, to enable it to be attached to a fluid container for example.

Further modifications of the invention within the scope of the claims would be apparent to a skilled person.

The invention claimed is:

1. A device for transferring a fluid to a fluid container, or from a fluid container, or both to and from a fluid container, wherein said fluid container comprises a sealing member having an innermost side and an outermost side, the device comprising:
   a piercing member having a tip for penetrating the sealing member;
   an elongated body defining a longitudinal flow channel through which a fluid may flow into and/or out of the fluid container, the elongated body having a greater width than the width of the piercing member;
   a plurality of openings that communicates with the flow channel and that is arranged to extend along at least 30% of the length (l) of the piercing member and each opening of the plurality of openings extends at least 50% of the maximum width of the piercing member to ensure that at least part of the plurality of openings is located substantially adjacent to the innermost side of said sealing member when the device is in use, each of the openings sized to allow a passage of liquids;
   an elastic retractable sleeve arranged to at least partly cover and seal the plurality of openings when the device has not been inserted into said sealing member of said fluid container, wherein said sleeve is arranged to abut against the outermost side of said sealing member when the device has been inserted into said sealing member of said fluid container and be retracted as the piercing member penetrates more deeply into said sealing member such that the retractable sleeve will cover and seal only a portion of the plurality of openings which are located outwards of the outermost side of the sealing member when the device is in use and thus prevent any fluid from leaking out of said plurality of openings; and an air inlet disposed on the elongated body.

2. The device according to claim 1, wherein the plurality of openings extends substantially along the entire length (l) of the piercing member.

3. The device according to claim 2, wherein the plurality of openings are uniformly spaced along the length (l) of the piercing member.

4. The device according to claim 1, wherein the plurality of openings are uniformly spaced along the length (l) of the piercing member.

5. The device according to claim 1, wherein the plurality of openings is arranged to extend along at least 50% of the length (l) of the piercing member.

6. The device according to claim 1 further comprising connecting means to connect it to the fluid container.

7. The device according to claim 6, wherein the connecting means comprises multiple resilient arms configured to slidably engage a rim on the fluid container.

8. The device according to claim 1 further comprising a ruled scale on the piercing member.

9. The device according to claim 1, wherein the plurality of openings is disposed behind the tip of the piercing member.

10. The device according to claim 1, wherein the plurality of openings is arranged to extend along at least 70% of the length (l) of the piercing member.

11. The device according to claim 10, wherein the plurality of openings are uniformly spaced along the length (l) of the piercing member.

12. A sealing member for sealing an inlet or an outlet of a fluid container, comprising a device that is integrally formed with the sealing member or releasably or non-releasably connected thereto, wherein said device comprises
a piercing member having a tip for penetrating the sealing member;
an elongated body defining a longitudinal flow channel through which a fluid may flow into and/or out of the fluid container, the elongated body having a greater width than the width of the piercing member;
a plurality of openings that communicates with the flow channel and that is arranged to extend along at least 30% of the length (l) of the piercing member and each opening of the plurality of openings extends at least 50% of the maximum width of the piercing member to ensure that at least part of the plurality of openings is located substantially adjacent to the innermost side of said sealing member when the device is in use, each of the openings being sized to allow for passage of liquids;
an elastic retractable sleeve arranged to at least partly cover and seal the plurality of openings when the device has not been inserted into said sealing member of said fluid container, wherein said sleeve is arranged to abut against the outermost side of said sealing member when the device has been inserted into said sealing member of said fluid container and be retracted as the piercing member penetrates more deeply into said sealing member such that the retractable sleeve will cover and seal only a portion of the plurality of openings which are located outwards of the outermost side of the sealing member when the device is in use and thus prevent any fluid from leaking out of said plurality of openings; and
an air inlet disposed on the elongated body.

13. The sealing member according to claim 12, wherein the device is slidably mounted on the sealing member so that the plurality of openings of the device may be opened and closed by sliding the device back and forth with respect to the sealing member.

14. A fluid container, comprising a sealing member according to claim 12 or 13.

15. The device according to claim 12, wherein said device is releasably connected to said sealing member.

16. The device according to claim 15, wherein the plurality of openings are uniformly spaced along the length (l) of the piercing member.

17. The device according to claim 15, further comprising connecting means to connect it to the fluid container.

18. The device according to claim 12, wherein said sealing member is a rubber, plastic, or elastomeric bung, stopper, membrane, or puncturable.

19. A device for transferring a fluid to a fluid container, or from a fluid container, or both to and from a fluid container, wherein said fluid container comprises a sealing member having an innermost side and an outermost side, the device comprising:
a piercing member having a tip for penetrating the sealing member;
an elongated body defining a longitudinal flow channel through which a fluid may flow into and/or out of the fluid container, the elongated body having a greater width than the width of the piercing member;
an opening that communicates with the flow channel and that is arranged to extend along at least 30% of the length (l) of the piercing member and the opening extends at least 50% of the maximum width of the piercing member to ensure that at least part of the opening is located substantially adjacent to the innermost side of said sealing member when the device is in use;
an elastic retractable sleeve arranged to at least partly cover and seal the opening when the device has not been inserted into said sealing member of said fluid container, wherein said sleeve is arranged to abut against the outermost side of said sealing member when the device has been inserted into said sealing member of said fluid container and be retracted as the piercing member penetrates more deeply into said sealing member such that the retractable sleeve will cover and seal only a portion of the opening which is located outwards of the outermost side of the sealing member when the device is in use and thus prevent any fluid from leaking out of the opening; and
an air inlet disposed on the elongated body.

* * * * *